(12) United States Patent
Madaus et al.

(10) Patent No.: US 7,562,658 B2
(45) Date of Patent: Jul. 21, 2009

(54) HOLDING DEVICE FOR A RESPIRATORY MASK

(75) Inventors: Stefan Madaus, Krailling (DE); Harald Vögele, Gauting (DE)

(73) Assignee: MAP Medizin Technologie GmbH, Martinsried (DE)

( * ) Notice: Subject to any disclaimer, the term of this patent is extended or adjusted under 35 U.S.C. 154(b) by 958 days.

(21) Appl. No.: 10/333,020

(22) PCT Filed: Jun. 22, 2001

(86) PCT No.: PCT/EP01/07123

§ 371 (c)(1),
(2), (4) Date: Jun. 2, 2003

(87) PCT Pub. No.: WO02/07806

PCT Pub. Date: Jan. 31, 2002

(65) Prior Publication Data

US 2004/0025882 A1    Feb. 12, 2004

(30) Foreign Application Priority Data

Jul. 21, 2000   (DE) ................................. 100 35 946

(51) Int. Cl.
*A61M 16/00* (2006.01)
*A62B 7/06* (2006.01)

(52) U.S. Cl. ............................ 128/207.17; 128/206.11; 128/207.18; 128/206.27; 128/207.11; 128/206.13; 128/204.11; 128/204.12; 128/201.22; 2/6.2; 2/9; 2/410; 2/415; 2/417; 2/418; 2/422; 2/423; 2/425; 2/452

(58) Field of Classification Search ............ 128/206.27, 128/207.11, 207.17, 206.13, 204.11, 204.12, 128/207.18, 201.22; 2/6.2, 9, 410, 415, 417, 2/418, 422, 423, 425, 452
See application file for complete search history.

(56) References Cited

U.S. PATENT DOCUMENTS

| 1,081,745 A | 12/1913 | Johnston et al. |
| 1,084,596 A | 1/1914 | Alexander |
| 1,192,186 A | 7/1916 | Greene |

(Continued)

FOREIGN PATENT DOCUMENTS

DE    196 25 337    1/1998

(Continued)

OTHER PUBLICATIONS

International Search Report for PCT/EP01/07132, dated Nov. 6, 2001.

(Continued)

*Primary Examiner*—Patricia M Bianco
*Assistant Examiner*—Nihir Patel
(74) *Attorney, Agent, or Firm*—Nixon & Vanderhye P.C.

(57) ABSTRACT

A holding device for a respiratory mask, especially for use in the field of sleep medicine, includes a headband which, in an application position, extends from the forehead area of the patient to behind the ear area of the patient, whereby the headband is provided with a flexible reinforcing insert for reinforcing the headband in a lateral direction. This makes it advantageously possible to provide the mask retention forces, which are necessary for reliably applying a respiratory mask, in a manner that is very compatible with regard to ergonomics.

42 Claims, 6 Drawing Sheets

U.S. PATENT DOCUMENTS

| | | | |
|---|---|---|---|
| 1,610,793 A | 12/1926 | Kaufman | |
| 2,016,210 A * | 10/1935 | Mann | 2/171 |
| 2,259,817 A * | 10/1941 | Hawkins | 128/207.18 |
| 2,353,643 A * | 7/1944 | Bulbulian | 128/207.11 |
| 2,783,474 A * | 3/1957 | Campagna et al. | 2/171 |
| 2,837,090 A | 6/1958 | Bloom et al. | |
| 2,931,356 A | 4/1960 | Schwarz | |
| 3,056,402 A | 10/1962 | Dickinson | |
| 3,234,940 A * | 2/1966 | Morton, Jr. | 128/206.27 |
| 3,752,157 A * | 8/1973 | Malmin | 128/206.12 |
| 3,792,702 A | 2/1974 | Delest | |
| 4,018,221 A * | 4/1977 | Rennie | 128/207.18 |
| 4,274,406 A | 6/1981 | Bartholomew | |
| 4,414,973 A | 11/1983 | Matheson et al. | |
| 4,454,880 A | 6/1984 | Muto et al. | |
| 4,665,566 A * | 5/1987 | Garrow | 2/171 |
| 4,744,358 A * | 5/1988 | McGinnis | 128/207.17 |
| 4,774,946 A * | 10/1988 | Ackerman et al. | 128/207.18 |
| 4,782,832 A | 11/1988 | Trimble et al. | |
| 4,821,736 A * | 4/1989 | Watson | 600/532 |
| 4,910,804 A | 3/1990 | Lidgren | |
| 4,919,128 A | 4/1990 | Kopala et al. | |
| 4,944,310 A | 7/1990 | Sullivan | |
| 4,960,121 A | 10/1990 | Nelson | |
| 5,069,205 A | 12/1991 | Urso | |
| 5,243,971 A | 9/1993 | Sullivan et al. | |
| 5,245,995 A | 9/1993 | Sullivan et al. | |
| 5,311,862 A | 5/1994 | Blasdell et al. | |
| 5,349,949 A | 9/1994 | Schegerin | |
| 5,441,046 A | 8/1995 | Starr et al. | |
| 5,481,763 A | 1/1996 | Brostrom et al. | |
| 5,533,506 A | 7/1996 | Wood | |
| 5,535,739 A | 7/1996 | Rapoport et al. | |
| 5,570,689 A * | 11/1996 | Starr et al. | 128/207.11 |
| 5,657,752 A | 8/1997 | Landis et al. | |
| 5,687,715 A * | 11/1997 | Landis et al. | 128/207.18 |
| 5,697,363 A | 12/1997 | Hart | |
| 5,704,345 A | 1/1998 | Berthon-Jones | |
| 5,709,204 A | 1/1998 | Lester | |
| 5,724,965 A | 3/1998 | Handke et al. | |
| 5,884,624 A | 3/1999 | Barnett et al. | |
| 5,921,239 A | 7/1999 | McCall et al. | |
| 5,979,133 A | 11/1999 | Funkhouser | |
| 6,012,455 A | 1/2000 | Goldstein | |
| 6,112,746 A | 9/2000 | Kwok et al. | |
| 6,119,693 A | 9/2000 | Kwok et al. | |
| 6,119,694 A | 9/2000 | Correa | |
| 6,192,886 B1 | 2/2001 | Rudolph | |
| 6,196,223 B1 | 3/2001 | Belfer et al. | |
| 6,269,814 B1 | 8/2001 | Blaszczykiewicz et al. | |
| 6,332,465 B1 * | 12/2001 | Xue et al. | 128/207.11 |
| 6,338,342 B1 | 1/2002 | Fecteau et al. | |
| 6,347,631 B1 | 2/2002 | Hansen et al. | |
| 6,357,441 B1 | 3/2002 | Kwok et al. | |
| 6,374,826 B1 | 4/2002 | Gunaratnam et al. | |
| 6,412,487 B1 | 7/2002 | Gunaratnam et al. | |
| 6,422,238 B1 | 7/2002 | Lithgow | |
| 6,439,230 B1 | 8/2002 | Gunaratnam et al. | |
| 6,467,483 B1 | 10/2002 | Kopacko et al. | |
| 6,470,886 B1 * | 10/2002 | Jestrabek-Hart | 128/207.11 |
| 6,478,026 B1 | 11/2002 | Wood | |
| 6,490,737 B1 | 12/2002 | Mazzei et al. | |
| 6,491,034 B1 | 12/2002 | Gunaratnam et al. | |
| 6,494,207 B1 * | 12/2002 | Kwok | 128/207.11 |
| 6,513,526 B2 | 2/2003 | Kwok et al. | |
| 6,516,802 B2 | 2/2003 | Hansen et al. | |
| 6,532,961 B1 | 3/2003 | Kwok et al. | |
| 6,550,070 B2 | 4/2003 | Weigand | |
| 6,561,190 B1 | 5/2003 | Kwok | |
| 6,565,461 B1 * | 5/2003 | Zatlin | 473/446 |
| 6,595,215 B2 | 7/2003 | Wood | |
| 6,610,032 B1 * | 8/2003 | Prody | 604/179 |
| 6,619,288 B2 | 9/2003 | Demers et al. | |
| D486,907 S | 2/2004 | Guney et al. | |
| 6,691,314 B1 | 2/2004 | Grilliot et al. | |
| 6,691,707 B1 | 2/2004 | Gunaratnam et al. | |
| 6,776,162 B2 | 8/2004 | Wood | |
| 6,796,308 B2 | 9/2004 | Gunaratnam et al. | |
| 6,807,967 B2 | 10/2004 | Wood | |
| 6,860,268 B2 | 3/2005 | Bohn et al. | |
| 6,907,882 B2 | 6/2005 | Ging et al. | |
| 6,997,187 B2 | 2/2006 | Wood et al. | |
| 7,000,613 B2 | 2/2006 | Wood et al. | |
| 7,047,972 B2 | 5/2006 | Ging et al. | |
| 7,152,599 B2 | 12/2006 | Thomas | |
| 7,210,481 B1 | 5/2007 | Lovell et al. | |
| 2001/0020474 A1 | 9/2001 | Hecker et al. | |
| 2001/0032648 A1 | 10/2001 | Jestrabek-Hart | |
| 2002/0023649 A1 | 2/2002 | Gunaratnam et al. | |
| 2002/0023650 A1 | 2/2002 | Gunaratnam et al. | |
| 2002/0144684 A1 | 10/2002 | Moone | |
| 2003/0005931 A1 | 1/2003 | Jaffre et al. | |
| 2003/0196656 A1 | 10/2003 | Moore et al. | |
| 2003/0196657 A1 | 10/2003 | Ging et al. | |
| 2003/0196658 A1 | 10/2003 | Ging et al. | |
| 2003/0196662 A1 | 10/2003 | Ging et al. | |
| 2004/0025882 A1 | 2/2004 | Madaus et al. | |
| 2004/0045551 A1 | 3/2004 | Eaton et al. | |
| 2004/0067333 A1 | 4/2004 | Amarasinghe | |
| 2004/0182397 A1 | 9/2004 | Wood | |
| 2005/0028821 A1 | 2/2005 | Wood et al. | |
| 2005/0028822 A1 | 2/2005 | Sleeper et al. | |
| 2005/0076913 A1 | 4/2005 | Ho et al. | |
| 2005/0155604 A1 | 7/2005 | Ging et al. | |
| 2005/0199241 A1 | 9/2005 | Ging et al. | |
| 2006/0081250 A1 | 4/2006 | Bordewick et al. | |
| 2006/0150982 A1 | 7/2006 | Wood | |
| 2006/0162729 A1 | 7/2006 | Ging et al. | |
| 2006/0272645 A1 | 12/2006 | Ging et al. | |

FOREIGN PATENT DOCUMENTS

| | | |
|---|---|---|
| DE | 19625337 | 1/1998 |
| DE | 29923126 | 5/1999 |
| DE | 199 62 515 | 7/2001 |
| DE | 10035946 | 2/2002 |
| EP | 29923126 U | 5/1999 |
| EP | 0958841 | 11/1999 |
| EP | 1027905 | 8/2000 |
| EP | 1099452 | 5/2001 |
| EP | 1118346 | 7/2001 |
| EP | 1258266 | 11/2002 |
| EP | 1314446 | 5/2003 |
| EP | 1334742 | 8/2003 |
| FR | 2618340 | 1/1989 |
| FR | 2720280 | 12/1995 |
| FR | 2735030 | 12/1996 |
| GB | 792 377 A | 3/1958 |
| GB | 799225 | 8/1958 |
| GB | 880942 | 10/1961 |
| GB | 2264646 | 9/1993 |
| GB | 2379886 | 3/2003 |
| WO | WO 00/78381 | 12/0000 |
| WO | WO 87/01950 | 4/1987 |
| WO | WO 98/04310 | 2/1998 |
| WO | WO 98/12965 | 4/1998 |
| WO | WO 99/04842 | 2/1999 |
| WO | WO 99/06116 A | 2/1999 |
| WO | WO 99/61088 | 12/1999 |
| WO | WO 00/69521 | 11/2000 |
| WO | WO 00/74758 A1 | 12/2000 |
| WO | WO 00/78383 | 12/2000 |
| WO | WO 00/78384 | 12/2000 |
| WO | WO 01/32250 | 5/2001 |

| WO | WO 01/62326 | 8/2001 |
| WO | WO 01/97892 | 12/2001 |
| WO | WO 02/07806 | 1/2002 |
| WO | WO 02/11804 | 2/2002 |
| WO | WO 02/47749 | 6/2002 |
| WO | WO 2004/041341 | 5/2004 |
| WO | WO 2004/073778 | 9/2004 |
| WO | WO 2005/014080 | 2/2005 |
| WO | WO 2005/016402 | 2/2005 |
| WO | WO 2005/016407 | 2/2005 |
| WO | WO 2005/018523 | 3/2005 |
| WO | WO 2005/063328 | 7/2005 |
| WO | WO 2005/079726 | 9/2005 |
| WO | WO 2005/097247 | 10/2005 |
| WO | WO 2006/044118 | 4/2006 |
| WO | WO 2006/044120 | 4/2006 |
| WO | WO 2006/096924 | 9/2006 |
| WO | WO 2006/130903 | 12/2006 |

OTHER PUBLICATIONS

German Search Report for DE 100 35 946.9, dated Apr. 6, 2001.
Examiner's Report mailed Mar. 26, 2007 for co-pending AU application No. 2007100138, 2 pages.
Brochure for Adam® CPAP Circuits, Airway Delivery And Management, Puritan Bennett, Apr. 1993, 1 page.
Brochure for ComfortLite™ Nasak Mask, Part Number and Order Guide, Respironics®, Feb. 2004, 2 pages.
Specification Sheet for Infinity™ 481 Direct Nasal Mask, Fisher & Paykel Healthcare, 2004, 2 pages.
Specificaiton Sheet for Opus Nasal Pillows Mask, Fisher & Paykel Healthcare, 2007, 2 pages.
U.S. Appl. No. 60/424,694, filed Nov. 8, 2002, Amarasinghe et al.
U.S. Appl. No. 60/488,810, filed Jul. 22, 2003, Gunaratnam et al.
U.S. Appl. No. 60/492,282, filed Aug. 5, 2003, Wood.
U.S. Appl. No. 60/493,325, filed Aug. 8, 2003, wood.
U.S. Appl. No. 60/494,119, filed Aug. 12, 2003, Gunaratnam et al.
U.S. Appl. No. 60/496,059, filed Aug. 18, 2003, Ho.
U.S. Appl. No. 60/501,028, filed Sep. 9, 2003, Wood.
U.S. Appl. No. 60/529,696, filed Dec. 16, 2003, Lithgow et al.
U.S. Appl. No. 60/533,124, filed Dec. 31, 2003, Drew.
U.S. Appl. No. 60/560,610, filed Apr. 9, 2004, Gunaratnam.
U.S. Appl. No. 60/619,426, filed Oct. 15, 2004, Bordewick.
U.S. Appl. No. 60/632,193, filed Jun. 6, 2005, Lubke et al.
U.S. Appl. No. 60/687,453, filed Jun. 6, 2005, Lubke et al.
U.S. Appl. No. 60/702,581, filed Jul. 27, 2005, Lubke et al.
U.S. Appl. No. 60/795,562, filed Apr. 28, 2006, Lubke et al.
U.S. Appl. No. 11/698,066, filed Jan. 26, 2007, Ging et al.
European Search Report for EP 03252555.2, dated Jan. 13, 2004, 5 pages.
International Search Report for PCT/EP01/07132, Mailed Nov. 6, 2001, 3 pages.
German Search Report for DE 100 35 946.9, dated Apr. 6, 2001, 4 pages.
European Search Report for EP 03 25 2573, Mailed Jan. 13, 2004, 6 pages.
European Search Report for EP 03 25 2554, Mailed Sep. 22, 2003, 3 pages.
European Search Report for EP 03 25 2572, mailed Jan. 13, 2004, 5 pages.
Gray's Anatomy, pp. 546, 547, 550 and 1631 (3 pages) (1995).
Ging et al., U.S. Appl. No. 10/391,440, Office Action Mailed Oct. 3, 2007, 12 pages.
Madaus et al., U.S. Appl. No. 10/333,020, Office Action Mailed Jul. 25, 2007, 19 pages.
Ging et al., U.S. Appl. No. 10/390,720, Office Action Mailed May 1, 2007, 24 pages.
Moore et al., U.S. Appl. No. 10/390,682, Office Action Mailed Feb. 20, 2007, 12 pages.
Ging et al., U.S. Appl. No. 11/795,606, filed Jul. 19, 2007.

* cited by examiner

HOLDING DEVICE FOR A RESPIRATORY MASK

CROSS REFERENCE TO RELATED APPLICATIONS

This application is the National Phase of International Application PCT/EP01/07132, filed Jun. 22, 2001 and that International Application was not published under PCT Article 21(2) in English.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention refers to a holding device for a respiratory mask, as it may for instance be used in the field of sleep medicine for fixing a nasal mask to the face of a patient.

2. Description of Related Art

Known holding devices of the above-mentioned kind usually comprise an upper belt arrangement and a lower belt arrangement, which are joined through a web arrangement arranged in the application position of the holding device at the back head portion of the patient. The two belt arrangements are made of a flexible textile material. In the area of the free end portions of the upper and lower belt arrangement, Velcro fastener means are provided through which the effective length and thus the press-on pressure of the respiratory mask against the face of the patient can be adjusted depending on the respective need. The upper belt arrangement may be connected in certain mask types with a forehead holding device so that the press-on pressure of the forehead rest element against the forehead of the patient can be defined by adjusting the effective length of the upper belt arrangement.

Depending on required therapeutic pressure of the respiratory gas supplied via the respiratory mask and depending on the individual face structure of the patient, mask press-on forces are partially required, which leave visible marks after a longer application of the mask on the face of the patient or in the forehead area.

BRIEF SUMMARY OF THE INVENTION

The invention is based on the object to provide a manageable holding device for a respiratory mask through which a desired respiratory mask press-on force by obtaining an improved wearing comfort can be exerted in a reliable manner.

This object is solved according to the invention by a holding device for a respiratory mask by the features defined in claim 1.

Thereby it becomes possible in an advantageous manner to fix the respiratory mask at low tension forces on the face of the patient. For the case that e.g. due to an increased internal mask pressure, the mask tends to lift off the patient's face, a correspondingly greater mask fixing force is automatically exerted.

An extremely reliable fixing of the forehead rest element in the forehead portion of the patient is achieved in an advantageous manner without significant tensile forces being exerted on the belt arrangement extending across the forehead and the back of the head.

An embodiment that is especially advantageous in view of an especially high wearing comfort is given in that the upper belt arrangement is formed with a waist in a manner that it extends from the forehead portion to the respective ear portion of the patient, and then takes a course diverging in the area of the ears towards the parting, and directly behind the ears descends and encompasses the back head portion of the patient in the area of the neck or approximately on the level of the patient's nose.

The flexible insert provided in the holding device may for instance be made of a thermoplastic plastic material layer having a thickness of 0.8 to 1.5 mm. A pad support is arranged in an area provided between the tensile-rigid inset and the patient. This pad support is according to an especially preferred embodiment of the invention formed by a thin and locally stitched foam layer on whose outer side a web material is backed. This web material may be a textile material or for instance a washable material to be wet-cleaned.

The headband arrangement of the respiratory mask is preferably provided with an adjustment means through which the effective length of the headband can be adjusted variably. The adjustment means may also be formed by a lock/clamping shift mechanism and/or by a Velcro fastener means.

According to an especially preferred embodiment of the invention, the flexible layer is formed of a plastic material, e.g. of a thermoplastic plastic material. As an alternative hereto or in combination therewith, it is also possible to make the flexible layer of a metal material, e.g. of a thin spring steel sheet. The bending elasticity of the flexible layer may be affected in a defined way by punchings or deep drawing structures. The flexible layer is, according to an especially preferred embodiment of the invention, punched out of a corresponding web material by means of a punching process. As an alternative, it is also possible to make the flexible layer by means of a plastic shaping process, e.g. of a thermoplastic material in an injection tool. It is also possible to provide especially reinforcing or functional structures on the mask holding device.

According to an especially preferred embodiment of the invention, the flexible layer is made of a thermo-formable material. Thereby it becomes possible in an advantageous manner to adapt the headband heated to a temperature of 60° C. individually to the patient, wherein the headband after cooling to ambient temperature may keep an advantageous spatial shape in view of a possible low surface pressure.

An embodiment that is especially advantageous in view of an especially high wearing comfort is provided in that the headband section is provided with a padding means. The padding means may preferably be formed of an open-cell foamed foam material. The padding means is preferably provided with a textile or washable layer. By the formation of locally stitched sections, the padding behavior of the padding means may be adapted in an advantageous manner.

An embodiment of the invention that is especially advantageous in view of an especially reliable fixing of the respiratory mask on the headband is given in that the holding device is provided—at least section-wise—with one of the two complementary structures of a Velcro fastening means. For this purpose, the headband is formed in a multi-layered backed manner. Thus, the flexible layer possibly provided with breakthroughs may for instance form the core portion of the headband, wherein a padding and a cover layer chosen with respect to structure and color are backed on the side facing the head of the patient in the application position of the headband.

An embodiment that is advantageous in view of an especially high wearing comfort is given in that the headband section has, seen in application position, an extension directed from the forehead portion to the upper ear portion, and an extension locally drawn up in the ear portion, wherein the headband portion directly after the ear portion has an extension descending towards the back of the head.

The above-mentioned object is solved according to a further solution idea by a holding device for a respiratory mask, having an element of increased flexural strength extending from the forehead portion laterally to the upper ear portion, and a bracket section descending behind the ear towards the neck, and a means for supporting the bracket section in the back head portion.

Thus, it becomes possible in an advantageous manner to apply a respiratory mask in a comfortable manner and possibly to refrain from using a belt arrangement.

The element of increased flexural strength may for instance be made of a wire material, in particular of a spring steel material. In an advantageous manner the element of increased flexural strength has a section projecting towards the nose tip of the patient that urges the respiratory mask against the face of the patient.

The introduction of forces into the respiratory mask is preferably implemented in that a deformation axis extends through a point of gravity of the mask support surface.

The support on the back of the head is preferably implemented by a padded band element in a manner that a deformation axis is defined which basically corresponds to the deformation axis acting on the mask.

BRIEF DESCRIPTION OF THE SEVERAL VIEWS OF THE DRAWING(S)

Further details can be derived from the following description in connection with the drawing.

DETAILED DESCRIPTION OF ILLUSTRATED EMBODIMENTS

Figure 1:
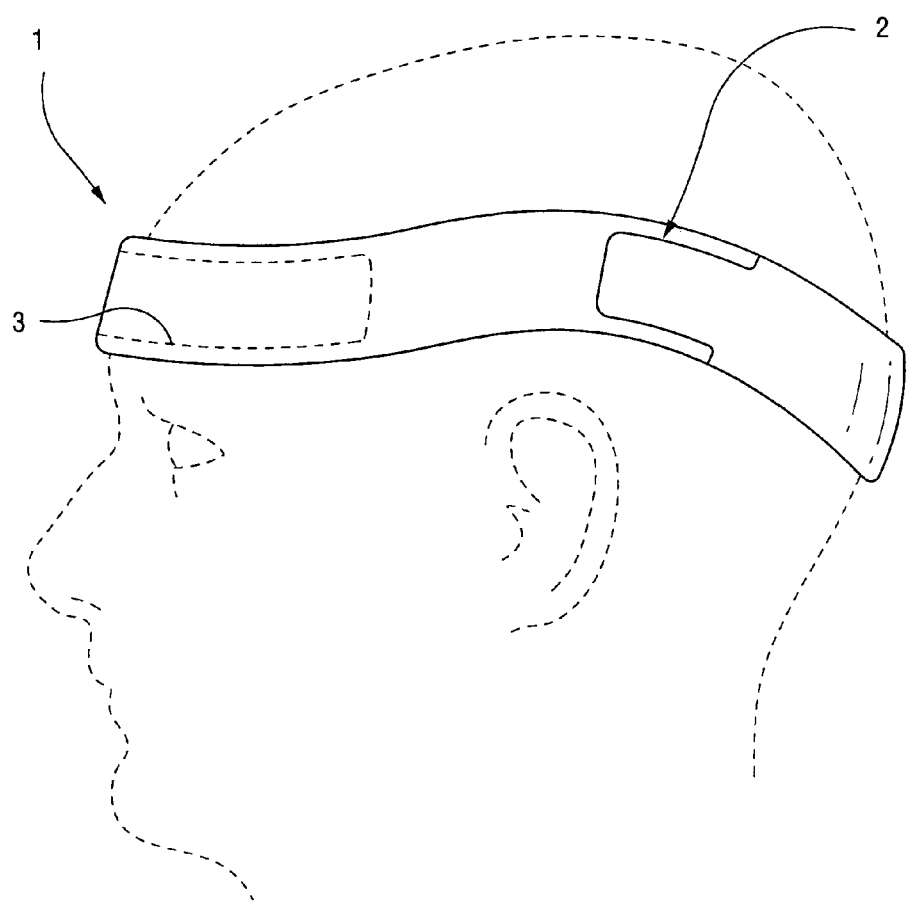
FIG. 1 shows a simplified view to explain the application position of a holding device for a respiratory mask according to a first preferred embodiment of the invention.

FIG. 1 shows a first preferred embodiment of a holding device for a respiratory mask, which comprises a headband section 1, which is laterally reinforced by a layer flexible in the winding direction. The headband section 1 extends in the application position from the forehead portion of the patient around the back head portion of the patient. To adapt the effective length of the headband section 1 to the individual head circumference of the patient, an adjustment means 2 is provided, which in the embodiment shown is formed by a Velcro fastener means. The outer portion of the headband section 1 visible in this case is formed by a fleece material, which can be brought into an adhesive connection with corresponding complementary Velcro fastener structures. Thus, it becomes possible, in particular in the area indicated by the dotted lines 3 to fix a forehead rest element of a respiratory mask. It is possible by the flexible layer integrated into the headband to give the headband an arbitrary extension in the lateral direction. In the embodiment shown in this case, the headband extends from the front forehead portion towards the upper ear portion and above the ear it has an extension diverging towards the top. In its further extension towards the back head portion, the headband descends towards the neck.

Figure 2:
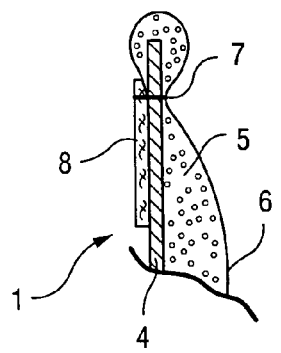
FIG. 2 shows a simplified sectional view to explain a preferred internal structure of a holding device for a respiratory mask with a flexible inset that is has lateral flexural strength.

FIG. 2 shows a simplified sectional view through a section of the headband 1.

The headband 1 has a reinforcement layer 4 (also referred to as a reinforcement insert) which is formed in this case of a thermoplastic material, the thickness of the reinforcement insert being in this case 0.75 mm. On the side of the reinforcement insert 4 facing the patient in the application position, a padding 5 is provided, which in this case is formed of an open-cell foamed foam material. The padding 5 in turn is covered by a cover layer 6 which is formed in this case by a textile material. The cover layer 6 and the padding 5 are coupled via a connection point 7 with the flexible layer. The connection point 7 is in this case formed by a stitching seam.

The padding 5 and a section of the cover layer are guided around a lateral edge of the reinforcement layer 4. This leads to an especially advantageous padding of the lateral edge of the reinforcement insert 4. The section guided around the reinforcement insert 4 is sewed onto the reinforcement insert 4 by means of said stitching seam. The stitching seam extends in the embodiment shown through a fleece material 8, which points towards the outside in the application position of the headband. The fleece material 8 is additionally directly adhered onto the reinforcement insert 4.

Figure 3:
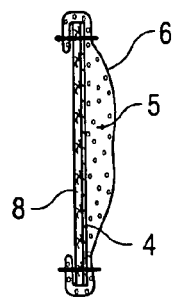
FIG. 3 shows a further, simplified sectional view to explain the inner structure of a further preferred embodiment of the holding device for a respiratory mask, also having a flexible insert.

FIG. 3 shows a further embodiment of the headband. Here, the padding body 5 is backed onto the reinforcement insert during a flame backing process. A fleece material layer 8 is provided on the rear side of the reinforcement insert 4 similar to the embodiment according to FIG. 2. The fleece material layer 8 is formed with respect to its layer thickness in a manner that a sufficient padding effect is achieved also towards the outside due to the fleece material layer 8. If needed, a padding may also be provided between the fleece material layer 8 and the reinforcement insert 4. In the embodiment shown in FIG. 3, the lateral edges of the reinforcement insert 4 are also lined by the material of a cover layer, which is guided around the lateral edges of the reinforcement insert and which is fixed by stitching seams.

Figure 4:
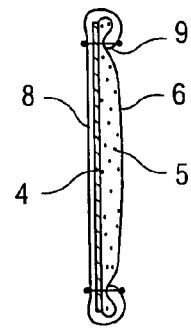
FIG. 4 shows a simplified sectional view through a holding device for a respiratory mask according to a fourth preferred embodiment having a padded circumferential edge stitched by a stitching seam.

The embodiment of the headband shown in FIG. 4 also comprises a reinforcement insert 4 and a fleece material layer 8 provided on the outwardly pointing side of the headband, said fleece material layer being guided around the lateral edge portion of the reinforcement insert 4 and which is fixed on the sides of the padding 5 together with a cover layer 6. The fixing is made preferably by stitching seams 9 that are shown in a highly magnified manner.

Figure 5:
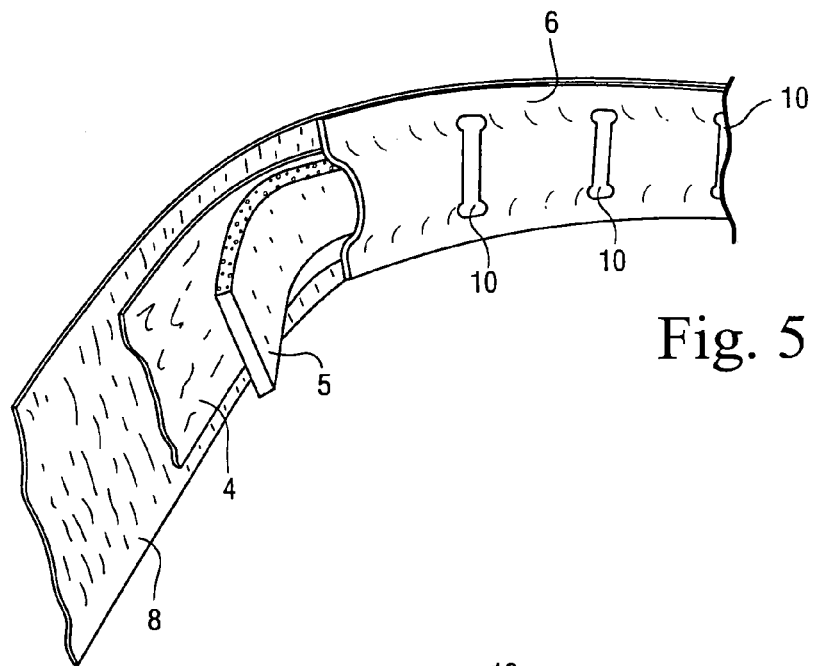
FIG. 5 shows a perspective view of a section of a holding device for a respiratory mask with a flexible inset that has flexural strength in the lateral direction and that has an integrated padding means.

FIG. 5 shows in a partially broken-up view a section of a headband according to the invention. The headband shown in this Figure again comprises a flexible reinforcement insert 4, which reinforces the headband against a bending around an axis perpendicularly to the headband rest surface. The flexible layer 4 is embedded between the rear cover layer, which is formed e.g. by the fleece material 8, and the inner cover layer 6 by interposition of the padding body 5. Stitching points 10 can be formed preferably by a thermo-welding process on the inner side of the headband, said stitching points providing the padding with a certain pre-load. The stitching points can for instance be formed during an ultrasonic welding process or by a correspondingly heated punching tool. An embodiment of the headband that is especially inexpensive to manufacture is provided in that the two layers 6, 8, and possibly also the reinforcement insert 4, are also connected to one another by an adhesion process.

Figure 6:
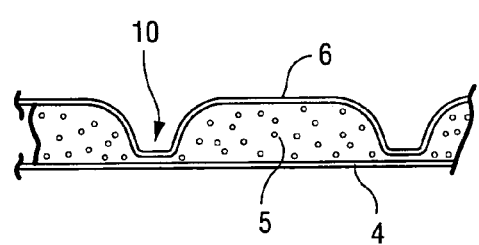
FIG. 6 shows a simplified detail sectional view to explain the stitching points formed by a melt-welding process on the inner side of the headband of the holding device.

A preferred embodiment of the stitching sections is shown in FIG. 6. As can be recognized, the cover layer 6 is welded onto the reinforcement layer 4 in the area of the welding points 10 through the hot-molten material of the padding 5.

Figure 7:
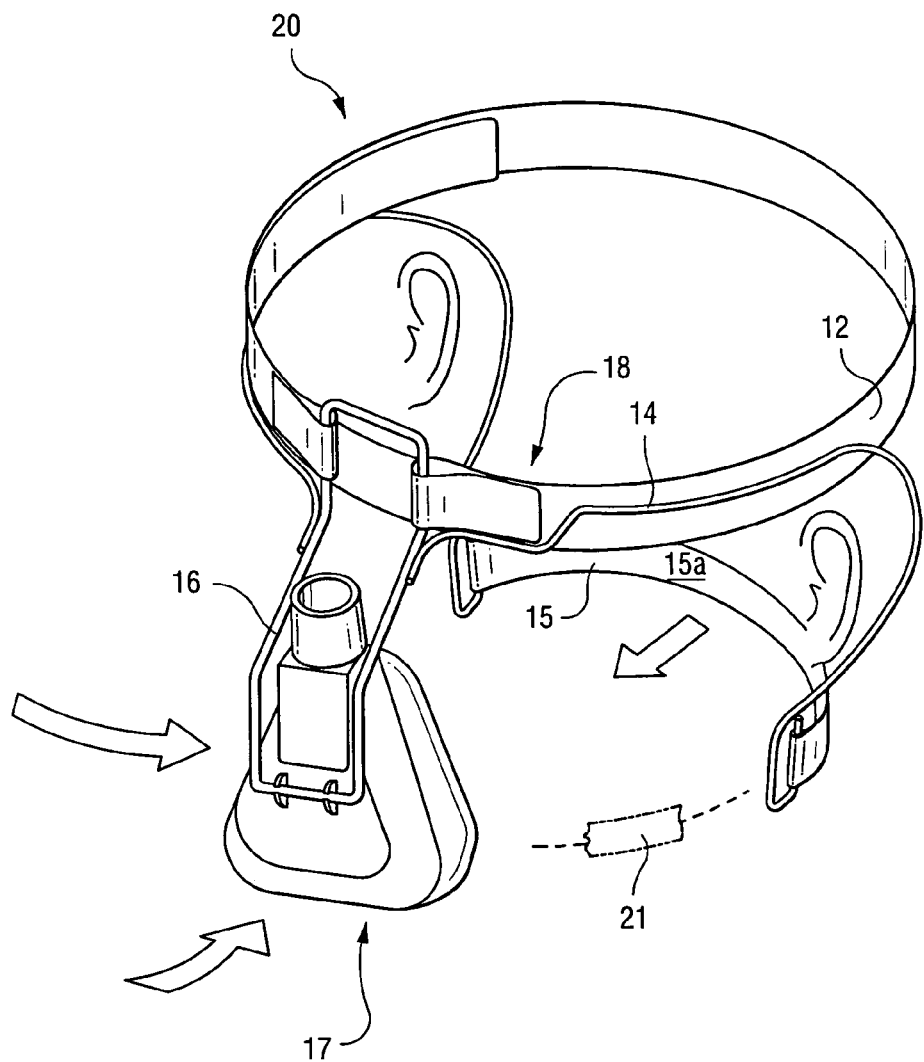
FIG. 7 shows a perspective view of a further embodiment of a holding device for a respiratory mask, in this case with a bracket element for exerting a respiratory mask press-on force.

FIG. 7 shows a further preferred embodiment of a holding device for a respiratory mask, which in this Figure comprises a headband 12, which is preferably in the same manner as the above-described headband 1 provided with an integral reinforcement layer. The headband 12 is provided with an element 14 having flexural strength, which extends in the application position of the holding device in a bracket-like descending manner behind the ear of the patient towards the neck portion. The element 14 having flexural strength may be supported via a support means 15 at the back head or neck portion of the patient. In the embodiment of the invention shown, the support means 15 is formed by a band element 15a that is longitudinally adjustable, which is coupled below the ear portion of the patient with the element 14 having flexural strength. A mask fixing means 16 is provided on the element 14 having flexural strength, said mask fixing means extending from the forehead portion to the nose tip of the patient. The mask fixing means 16 is coupled with a respiratory mask 17 in a section which basically extends in the area of the point of gravity that extends through the sealing pad of the facial rest zone defined by the respiratory mask. In the embodiment shown, the coupling of the respiratory mask 17 with the mask fixing means 16 is implemented in that the respiratory mask can be tilted to a certain extent. The arrangement is preferably adapted so that the deformation axis of the press-on force acting on the respiratory mask 17 substantially corresponds to the deformation axis caused by the support means 15 and the headband 12 themselves.

The element 14 having flexural strength is preferably releasably fixed to the headband 12 via a Velcro fastener means 18.

The mask fixing means 16 and the element 14 having flexural strength are made of a steel spring wire in the embodiment shown in this case.

The headband 12 further comprises quick acting closure means 20 through which the headband 12 can be expanded and shortened in a defined manner. In the embodiment shown it is possible to attach a further band element 21 (only indicated by way of a hint) to the element having flexural strength, by means of which said band element additional holding forces can be exerted in the fashion of a belt arrangement onto the respiratory mask 17.

Figure 8:
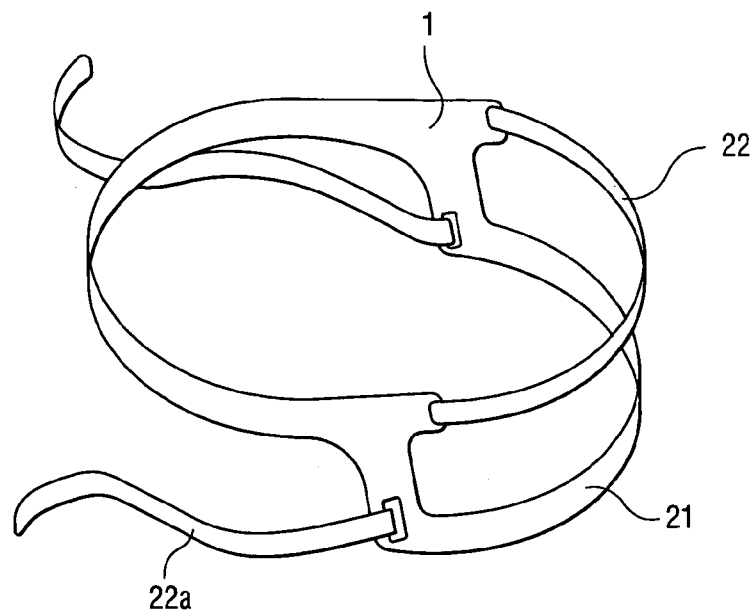
FIG. 8 shows a simplified perspective view of a further embodiment of a holding device for a respiratory mask having a reinforcement insert.

FIG. 8 shows a further embodiment of a holding device for a respiratory mask, which in turn comprises a headband 1, which is provided in the application surface with a substantially lateral reinforcement insert 4 which is of flexural strength and can be unwound in the circumferential direction. The headband 1 comprises in the application position behind the ear portion of the patient descending sections subsequently extending around the neck portion. An elastic band 22 is provided to fix the headband 1, said band extending around the back head portion of the patient. On the section of the headband 1 resting in the application position on the forehead of the patient, a forehead rest element of a respiratory mask arrangement may be fixed via a Velcro fastener means. Further forces may be exerted onto the respiratory mask via further lower belts 22a.

Figure 9:
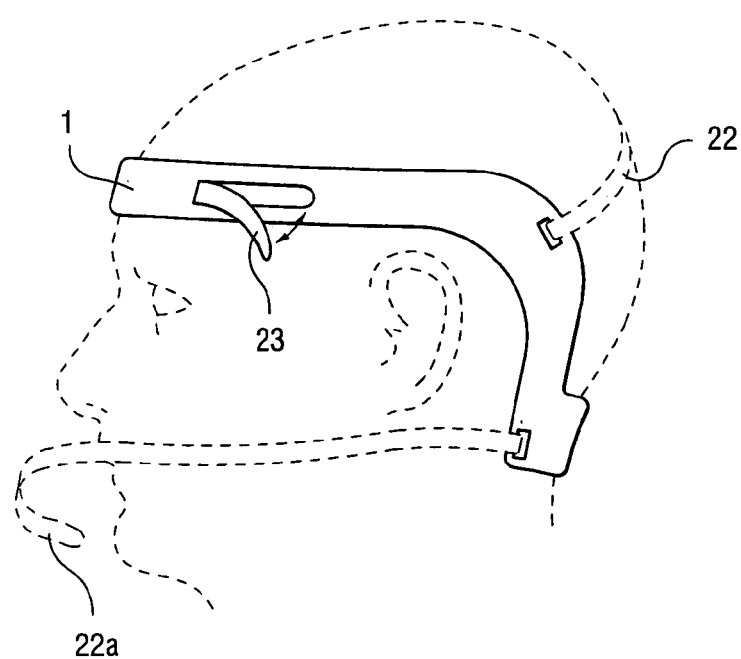
FIG. 9 shows a simplified view of the holding device, however basically with integrated forehead rest attachment flaps according to FIG. 8 in application position.

FIG. 9 shows as an example a holding means for a respiratory mask in the application position, the structure thereof basically corresponding to the holding device shown in FIG. 8. The holding device 1 extends from the forehead portion of the patient towards its upper ear portion and directly descends behind the ears of the patient towards the patient's neck. A respiratory mask (not shown in detail) may additionally be fixed via the lower belt arrangement 22a. By fixing the respiratory mask via the forehead rest element and the lower belt arrangement, an application of the respiratory mask advantageous in terms of ergonomics is obtained. The forehead support element of the respiratory mask (not shown) may be implemented via a Velcro fastener 23 shown in a simplified manner.

Figure 10:
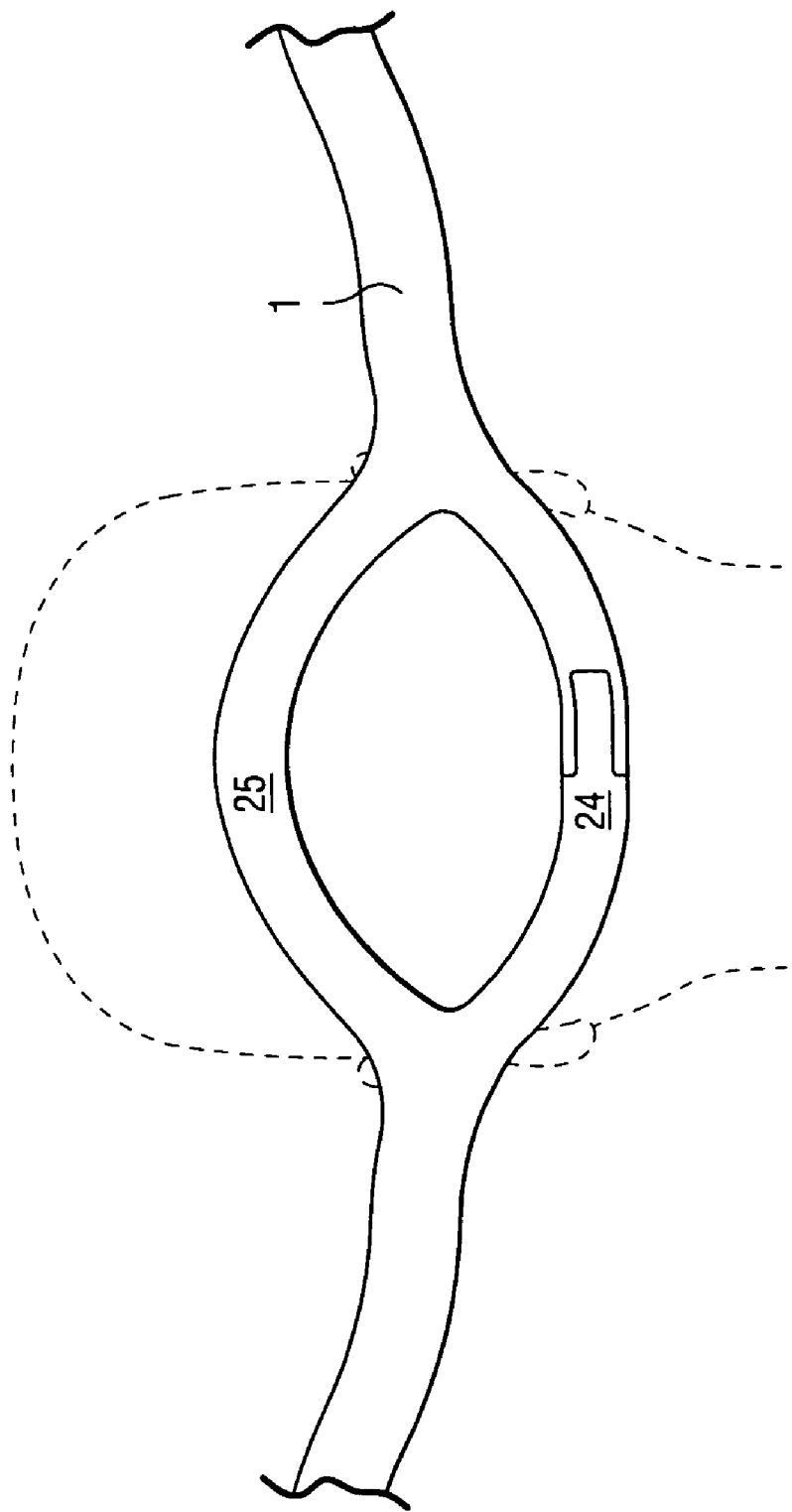
FIG. 10 shows a simplified view to explain a further embodiment of a holding device of a respiratory mask with a flexible reinforcement insert and an opening shown in this Figure in application position in the back head portion.

Instead of the elastic tension 22 provided in the embodiment according to FIG. 8, it is also possible to design the holding device I in a manner that this holding device defines in the back head portion of the patient a larger opening and is supported via at least two back sections 25, 24 in the back head portion of the patient as shown in FIG. 10. The back head sections 25, 24 are preferably, as shown, adjustable in length.

Figure 11:
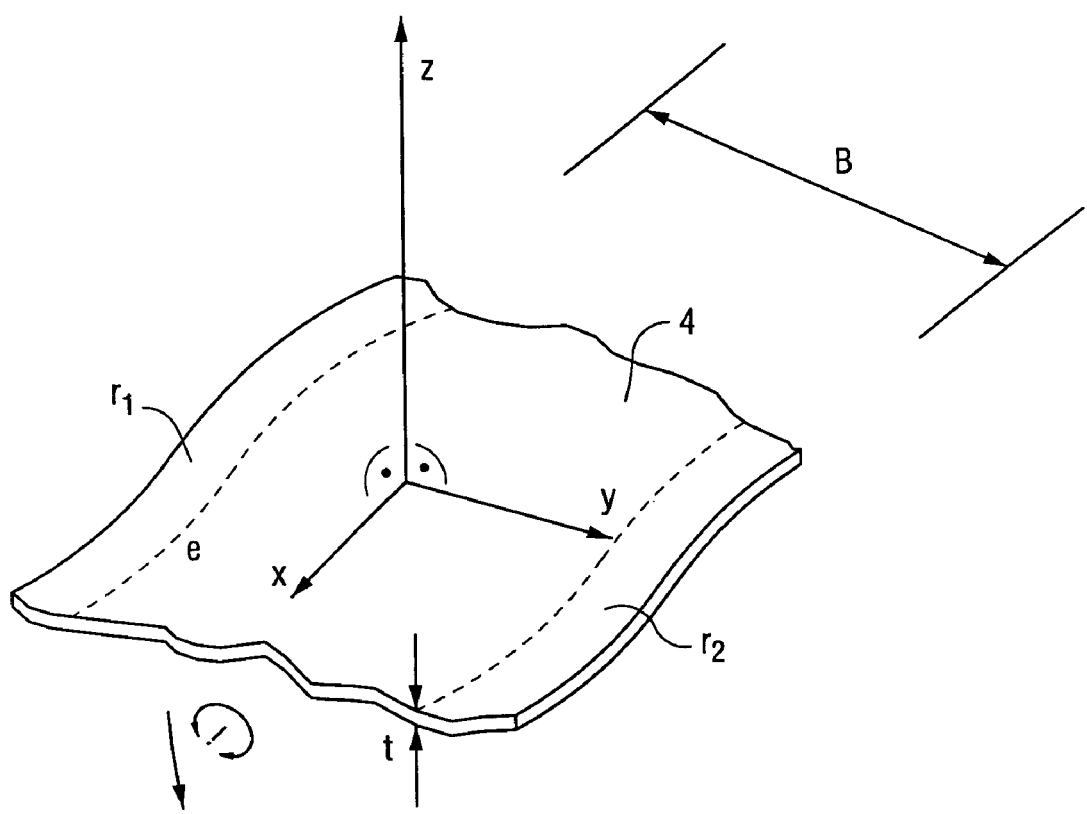
FIG. 11 is a principle sketch to explain the flexural strength of the flexible insert around their main axes.

FIG. 11 shows a basic sketch to explain the mechanical properties of the flexible reinforcement insert 4. The flexible reinforcement insert allows a bending strain around the main axes x and y extending in the main level 3 of the reinforcement insert 4. Deformations and reinforcement insert 4 around the main axis z extending perpendicularly to the level 3 are substantially avoided due to the large width of the reinforcement insert. The width B of the reinforcement insert 4 and the thickness t of the reinforcement insert 4 and the E-module E of the reinforcement insert 4 are preferably adapted such that the bending momentum around the main axis Z occurring during the application of the respiratory mask does not cause inadmissibly great deformations.

Since the flexural strength of the reinforcement layer 4 around the main axis Z is substantially defined by the edge zone portion r1, r2 of the reinforcement insert 4, it is possible to provide openings in the intermediate portion, so that the reinforcement insert 4 has a substantially latticework-like structure.

A latticework-like structure of the reinforcement insert 4 may in particular be realized in the manufacture of the reinforcement insert 4 by a plastic injection tool.

In zones of an especially high bending load it is also possible to provide a plurality of reinforcement inserts in the headband, or to form the reinforcement layers with locally thicker portions.

What is claimed is:

1. A holding device for a respiratory mask comprising:
   a headband section having a headband surface adapted to engage a patient in an application position from a forehead portion of the patient around a back head portion of the patient located behind the patient's ears;
   a reinforcement layer integrated into the headband section, the reinforcement layer adding flexural strength to the headband section to reinforce the headband section against bending around an axis substantially perpendicular to the headband surface; and
   a mask supporting arrangement provided to the headband section, the mask supporting arrangement structured to support the respiratory mask in an application position on the patient's face in use,
   wherein the headband section is provided with padding including a foam layer, which is located in the application position of the headband section between the reinforcement layer and the patient, and wherein the padding comprises stitched sections.

2. A holding device as claimed in claim 1, wherein the reinforcement layer is made of a flat plastic material.

3. A holding device as claimed in claim 1, wherein the reinforcement layer is made of a sheet strip.

4. A holding device as claimed in claim 1, wherein the reinforcement layer is made of a thermo-formable material.

5. A holding device as claimed in claim 1, wherein the headband section is provided with a hook and loop fastener fleece material.

6. A holding device as claimed in claim 1, wherein the headband section is formed in a multi-layered backed manner.

7. A holding device as claimed in claim 1, wherein the reinforcement layer is provided with breakthroughs.

8. A holding device as claimed in claim 1, wherein the headband section has an extension in the application direction directed from the forehead portion of the patient towards the upper ear portion and that it has a locally drawn-up extension descending in the back head portion.

9. A holding device for a respiratory mask as claimed in claim 1, wherein the stitched sections are formed by a thermal welding process.

10. A holding arrangement for a respiration mask comprising:
    a headband portion adapted to engage a patient in an application position from a forehead region of the patient to a back of the head region of the patient located behind the patient's ears,
    wherein the headband portion has at least one flexible and laterally substantially flexurally stiff reinforcing insert which allows bending deformation about x and y axes extending in a main surface of the reinforcing insert and substantially prevents bending deformation about a z axis extending perpendicular to the main surface for stiffening the headband portion in a lateral direction, and
    the headband portion includes a mask supporting arrangement structured to support the respiration mask in an application position on the patient's face in use,
    wherein the headband portion includes padding having a foam insert which in the application position of the headband portion is between the flexible reinforcing insert and the patient, and wherein the padding has stitched portions.

11. A holding arrangement according to claim 10, wherein the flexible reinforcing insert is formed from a flat plastic material.

12. A holding arrangement according to claim 10, wherein the flexible reinforcing insert is formed from a sheet metal strip.

13. A holding arrangement according to claim 10, wherein the flexible reinforcing insert is formed from a thermo-formable material.

14. A holding arrangement according to claim 10, wherein the headband portion is provided with a touch-and close fastener non-woven material.

15. A holding arrangement according to claim 10, wherein the headband portion is of a multi-layer lined configuration.

16. A holding arrangement according to claim 10, wherein the flexible reinforcing insert is provided with openings therethrough.

17. A holding arrangement according to claim 10, wherein the headband portion in the application position is of a configuration directed from the forehead region of the patient to the upper ear region, and in the ear region it is of a configuration which is locally raised and falls again in the region of the back of the head.

18. A holding arrangement according to claim 10, wherein the stitched portions are formed by a thermal welding operation.

19. A holding device as claimed in claim 1, wherein the mask supporting arrangement includes a fixing element extending from the headband section, the fixing element structured to support the respiratory mask in the application position on the patient's face in use.

20. A respiratory mask arrangement, comprising a respiratory mask having a forehead rest element, and
    the holding device as claimed in claim 1, wherein the mask supporting arrangement includes a hook and loop fastener structured to fix the forehead rest element of the respiratory mask.

21. A holding device as claimed in claim 1, wherein the mask supporting arrangement is provided to the headband section at a position along the forehead portion of the patient in use.

22. A holding arrangement according to claim 10, wherein the mask supporting arrangement includes a fixing element extending from the headband section, the fixing element structured to support the respiratory mask in the application position on the patient's face in use.

23. A respiratory mask arrangement, comprising a respiratory mask having a forehead rest element, and
    the holding arrangement according to claim 10, wherein the mask supporting arrangement includes a hook and loop fastener structured to fix the forehead rest element of the respiratory mask.

24. A holding arrangement according to claim 10, wherein the mask supporting arrangement is provided to the headband portion at a position along the forehead region of the patient in use.

25. A holding arrangement for a respiratory mask comprising:
    a band portion; and
    at least one flexible and laterally substantially flexurally stiff reinforcement provided to the band portion, said reinforcement being made of a thermoplastic plastic to allow bending deformation about x and y axes extending in a main surface of the reinforcement and to substantially prevent bending deformation about a z axis extending perpendicular to the main surface for stiffening the band portion in a lateral direction, wherein the band portion includes a fixing element extending from the band portion and structured to support the respiratory mask in an application position on the patient's face in use, the fixing element including first and second ends suspended from the band portion and a generally U-shaped continuous portion suspended between the ends that is adapted to be coupled with the respiratory mask.

26. A holding arrangement according to claim 25, wherein the reinforcement is formed from a flat plastic material.

27. A respiratory mask arrangement including a respiratory mask having a coupling member and the holding arrangement of claim 25.

28. A holding arrangement according to claim 25, wherein the band portion is provided with a padded section.

29. A holding arrangement according to claim 28, wherein the padded section includes a foam portion located between the reinforcement and the patient in use.

30. A holding arrangement according to claim 29, wherein the band portion includes a textile material layer positioned between the foam portion and the patient in use.

31. A holding arrangement according to claim 29, wherein the foam portion includes open cell foam.

32. A holding arrangement as claimed in claim 25, wherein the band portion and reinforcement are stitched to one another.

33. A holding arrangement as claimed in claim 25, wherein the reinforcement has a thickness in the range of about 0.8 to 1.5 mm.

34. A holding arrangement as claimed in claim 33, wherein a width of the reinforcement is much greater than its thickness.

35. A holding arrangement for a nasal seal, comprising:

a strap portion having a multi-layered construction including a foam padding layer and a textile layer, the textile layer being provided between the foam padding layer and the patient's skin and adapted to contact the patient's skin; and a fixing element extending from the strap portion and structured to support the nasal seal in an application position on the patient's face in use, the fixing element including first and second lateral portions suspended from the strap portion and a central portion between the lateral portions that is adapted to be coupled with the nasal seal, wherein the strap portion includes fastening portions structured to wrap around respective first and second lateral portions of the fixing element to releasably fix the fixing element to the strap portion, each of the fastening portions including hook and loop fasteners, and at least a portion of each lateral portion of the fixing element being positioned such that the foam padding layer is between the fixing element and the textile layer.

36. A respiratory mask arrangement, comprising a respiratory mask and the holding arrangement as claimed in claim 35.

37. A respiratory mask arrangement as claimed in claim 36, wherein the mask includes a frame and a nasal seal provided to the frame.

38. A respiratory mask arrangement, comprising:

a frame;

a seal provided to the frame;

a pair of fixing elements extending laterally away from the frame, each fixing element having a first end coupled to the frame and a second end including a slotted connector; and a multi-layered member positioned between the first and second ends of each of the fixing elements, each multi-layered member including a foam padding layer and a textile layer with the foam padding layer being provided between the textile layer and at least a portion of the fixing element.

39. A respiratory mask arrangement as claimed in claim 38, further comprising a headgear strap coupled with each slotted connector.

40. A respiratory mask arrangement as claimed in claim 39, wherein the multi-layered member is the headgear strap.

41. A respiratory mask arrangement as claimed in claim 38, wherein the textile layer is adapted to contact the patient's face.

42. A respiratory mask arrangement as claimed in claim 38, wherein the seal includes a nasal seal.

* * * * *